(12) United States Patent
Schneider (10) Patent No.: US 8,738,144 B2
(45) Date of Patent: May 27, 2014

(54) BIOELECTRIC IMPLANT AND METHOD

(75) Inventor: David J. Schneider, Lafayette, CO (US)

(73) Assignee: Ingenium, LLC, Lafayette, CO (US)

( * ) Notice: Subject to any disclaimer, the term of this patent is extended or adjusted under 35 U.S.C. 154(b) by 517 days.

(21) Appl. No.: 12/464,705

(22) Filed: May 12, 2009

(65) Prior Publication Data

US 2010/0292756 A1  Nov. 18, 2010

(51) Int. Cl.
*A61N 1/30* (2006.01)

(52) U.S. Cl.
USPC ............... 607/50; 607/51; 607/75; 607/149; 607/127; 607/132

(58) Field of Classification Search
USPC .................. 607/50, 51, 75, 149, 132, 127
See application file for complete search history.

(56) References Cited

U.S. PATENT DOCUMENTS

| | | |
|---|---|---|
| 3,345,989 A | 10/1967 | Reynolds |
| 3,353,539 A | 11/1967 | Preston |
| 3,421,512 A | 1/1969 | Frasier |
| 3,749,101 A | 7/1973 | Williamson |
| 3,842,843 A | 10/1974 | Mourot et al. |
| 3,897,267 A | 7/1975 | Tseung et al. |
| 4,195,367 A | 4/1980 | Kraus |
| 4,216,548 A | 8/1980 | Kraus |
| 4,652,459 A | 3/1987 | Engelhardt |
| 4,932,951 A | 6/1990 | Liboff et al. |
| 4,937,323 A | 6/1990 | Silver et al. |
| 5,067,940 A | 11/1991 | Liboff et al. |
| 5,112,337 A | 5/1992 | Paulos et al. |
| 5,123,898 A | 6/1992 | Liboff et al. |
| 5,195,542 A | 3/1993 | Gazielly et al. |
| 5,292,252 A | 3/1994 | Nickerson et al. |
| 5,306,278 A | 4/1994 | Dahl et al. |

(Continued)

FOREIGN PATENT DOCUMENTS

| | | |
|---|---|---|
| DE | 4233605 | 6/1994 |
| EP | 2409656 | 1/2012 |

OTHER PUBLICATIONS ezLoc Femoral Fixation Device, Bioment Sports Medicine, 2007, pp. 1-12.

(Continued)

*Primary Examiner* — Christopher D Koharski
*Assistant Examiner* — Natasha Patel
(74) *Attorney, Agent, or Firm* — Sheridan Ross PC (57) ABSTRACT

Bioelectric implants are provided in three distinct embodiments, namely a bone/tissue anchor, a suture construction, and a plate. The bioelectric implants function in dual capacities as both fixation devices, and as galvanic cells for the production of electrical energy used for therapeutic purposes in tissue regeneration and healing. The bioelectric anchor may take the general form of a screw or pin having a hollow interior or cavity that extends through the body of the anchor. A coating can be applied to the cavity to form the anode portion of the galvanic cell. The outer surface of the anchor serves as a cathode. Bodily fluids and tissue act as an electrolyte to facilitate the chemical reactions necessary for the galvanic cell. For the suture construction, one or more strands of material are the cathode, and one or more strands of peripheral surrounding material act as the anode. Bodily fluids/tissue in contact with the suture act as an electrolyte. The bioelectric plate can be used in combination with the bioelectric anchor to supplement delivery of electrical energy. The plate has anode and cathode portions also making it a source of electrical energy.

11 Claims, 5 Drawing Sheets

(56) References Cited

U.S. PATENT DOCUMENTS

| | | | |
|---|---|---|---|
| 5,324,323 A | 6/1994 | Bui | |
| 5,350,383 A | 9/1994 | Schmieding et al. | |
| 5,353,935 A | 10/1994 | Yeager et al. | |
| 5,383,935 A * | 1/1995 | Shirkhanzadeh | 623/23.49 |
| 5,395,382 A | 3/1995 | DiGiovanni et al. | |
| 5,433,735 A * | 7/1995 | Zanakis et al. | 607/50 |
| 5,441,508 A | 8/1995 | Gazielly et al. | |
| 5,458,558 A | 10/1995 | Liboff et al. | |
| RE35,129 E | 12/1995 | Pethica et al. | |
| 5,575,801 A | 11/1996 | Habermeyer et al. | |
| 5,681,333 A | 10/1997 | Burkhart et al. | |
| 5,725,377 A * | 3/1998 | Lemler et al. | 433/173 |
| 6,013,083 A | 1/2000 | Bennett | |
| 6,019,781 A | 2/2000 | Worland | |
| 6,206,886 B1 | 3/2001 | Bennett | |
| 6,214,049 B1 * | 4/2001 | Gayer et al. | 623/16.11 |
| 6,409,764 B1 | 6/2002 | White et al. | |
| 6,514,274 B1 | 2/2003 | Boucher et al. | |
| 6,616,665 B2 | 9/2003 | Grafton et al. | |
| 6,778,861 B1 | 8/2004 | Liebrecht et al. | |
| 6,828,908 B2 | 12/2004 | Clark | |
| 6,830,572 B2 | 12/2004 | Mcdevitt et al. | |
| 7,004,974 B1 | 2/2006 | Larsson et al. | |
| 7,172,594 B2 | 2/2007 | Biscup | |
| 7,230,153 B2 | 6/2007 | Flick | |
| 7,918,854 B2 * | 4/2011 | Schwartz | 606/65 |
| 7,935,116 B2 * | 5/2011 | Michelson | 606/60 |
| 7,938,847 B2 * | 5/2011 | Fanton et al. | 606/232 |
| 2004/0199166 A1 | 10/2004 | Schmieding et al. | |
| 2006/0078847 A1 | 4/2006 | Kwan | |
| 2006/0100629 A1 | 5/2006 | Lee | |
| 2006/0155384 A1 | 7/2006 | Ellingsen et al. | |
| 2006/0247641 A1 | 11/2006 | Re et al. | |
| 2007/0198087 A1 | 8/2007 | Coleman et al. | |
| 2007/0233128 A1 | 10/2007 | Schmieding et al. | |
| 2008/0015578 A1 | 1/2008 | Erickson et al. | |
| 2009/0099602 A1 * | 4/2009 | Aflatoon | 606/246 |
| 2009/0105753 A1 | 4/2009 | Greenhalgh et al. | |

OTHER PUBLICATIONS

Fleega, "Arthroscopic Transhumeral Rotator Cuff Repair: Giant Needle Technique", Arthroscopy Feb. 2002, 18(2):218-23.

Gonzalez-Lomas et al., "In situ transtendon repair outperforms tear completion and repair for partial articular-sided supraspinatus tendon tears", J Shoulder Elbow Surg 2008; 17:722-728.

Jiang, "Bioelectric Battery and Its Application", St. Jude Medical, Dec. 13, 2007.

Kim et al., "Arthroscopic Transosseous Rotator Cuff Repair", Orthopedics 2008, 31:327-30.

U.S. Appl. No. 12/358,953, filed Jan. 23, 2009, Schneider.

Locking Compression Plate (LCP) System, Synthes North America, 2009, available at http://us.synthes.com/Products/Trauma/Plate+and+Screw+Systems/Locking+Compression+Plate+%28LCP%29+System.htm, accessed Jun. 8, 2009, 1 page.

Meyer et al., "Association of osteopenia of the humeral head with full-thickness rotator cuff tears", JSES 2004: 13:333-7, Zurich and Bassersdorf, Switzerland.

International Search Report for International (PCT) Patent Application No. PCT/US2010/034468, mailed Jul. 15, 2010 3 pages.

Written Opinion for International (PCT) Patent Application No. PCT/US2010/034468, mailed Jul. 15, 2010 5 pages.

International Preliminary Report on Patentability for International (PCT) Patent Application No. PCT/US2010/034468, mailed Nov. 24, 2011 7 pages.

U.S. Appl. No. 13/958,401, filed Aug. 2, 2013, Schneider.

"ExpresSew™II Surgical Technique," DePuy Mitek, 2007, 8 pages.

"ExpresSew®III Flexible Suture Passer Surgical Technique Guide," DePuy Mitek, 2011, 8 pages.

"3.0 mm Headless Compression Screw," product literature, Synthes North America, 2009, 1 page.

* cited by examiner

BIOELECTRIC IMPLANT AND METHOD

FIELD OF THE INVENTION

The present invention relates generally to medical methods and apparatuses for repair and stabilization of damaged tissues, and more particularly, to orthopedic fixation implants that generate electrical energy to provide therapeutic benefits for healing of the affected tissues.

BACKGROUND OF THE INVENTION

It is well known to utilize a source of electrical power in order to speed the healing process in damaged bone and soft tissue. Through extensive research and development, it has been found that both electrical current and magnetic fields can play an important role in modifying tissue behavior. It is known that bone tissue generates its own electrical potentials during the healing process, and exposing the bone tissue to electrical energy at selected voltages and amperages can greatly enhance the speed of tissue regeneration.

Accordingly, a number of references disclose electrical implants that are used for various healing and regenerative purposes with respect to both bone and soft tissue. A typical electrical implant device includes probes or electrodes that are positioned adjacent the targeted tissue, and the electrodes are powered by an external power source, such as a subcutaneous battery. Discharged batteries must be replaced, and ultimately removed once the desired duration of electrical energy exposure has been achieved.

It is also known to utilize body fluids as an electrolyte in combination with anode and cathode elements implanted within the body to produce a galvanic cell capable of generating electrical potential for a specified treatment. Since the human body is mainly composed of water, even tissue and bone in contact with anode and cathode elements is sufficient for facilitating a galvanic reaction.

One early example of an electrical power source utilizing body fluids as an electrolyte is the U.S. Pat. No. 3,345,989. This reference discloses a pair of metal electrodes surgically implanted in body tissue in which one electrode acts as the anode and the other acts as the cathode. An implanted electronic device may close the circuit and therefore receive electrical power by use of insulated leads that extend from each electrode to the implanted device.

Another early example of an implanted device that acts as a bioelectric power supply is the invention found in the U.S. Pat. No. 3,421,512. This reference discloses an implanted pacemaker in which the electrical components are contained within a sealed housing formed by electrode plates that are sealed to one another. The electrode plates are made of selected materials to react with bodily fluids to form a galvanic power supply.

U.S. Pat. No. 3,353,539 discloses a biological power supply in which bodily fluid is used as the electrolyte to generate power from implanted electrodes. The electrodes are constructed of the similar metals resulting in production of electrical power.

U.S. Pat. No. 5,353,935 discloses a prosthetic implant for implantation into skeletal bone comprising an implantable base member having an internal housing surrounded partially by a porous wall, an anode secured in the internal housing in electrical contact with the porous wall, and a porous means placed in the internal housing for retaining a biocompatible electrolyte. When implanted into bone structure, the prosthetic implant generates sufficient current flow which results in in-vivo formation of calcium phosphate minerals between the implant and the surrounding bone, thereby, resulting in improved fixation and stability of the implant.

U.S. Pat. No. 5,725,377 discloses a dental implant that employs electrical bone growth stimulation by incorporating a galvanic cell in the implant. The implant is formed as a machine screw made of titanium. The machine screw contains an internal threaded portion for accommodating a cap screw to cover the top of the implant. The implant has a hollow portion with a small aluminum rivet pressed therein that makes intimate contact with the titanium implant. The rivet forms the anode of the cell which becomes the negative electrode of the battery. A slug of silver chloride is fastened to a cover screw. A saline solution is used as the electrolyte. Once activated, the reaction consists of the reduction of silver chloride to metallic silver. The slug of silver chloride forms the cathode of the cell and becomes the positive terminal of the battery.

U.S. Pat. No. 7,230,153 discloses a multi-layer conductive appliance having wound healing and analgesic properties. The appliance can be used as a wound dressing having at least one layer of a conductive material. When placed proximate to the portion of the body suffering from a pathologic condition, the dressing alters the electro-dynamic processes occurring in conjunction with the pathologic condition to promote healing and pain relief. The conductive material placed in contact with tissue surrounding the periphery of the wound and lowers the electrical potential and resistance of the wound thereby increasing wound current. Multi-laminate embodiments exhibit conductive material concentration gradients and a capacitive effect when sequential conductive layers are insulated by intervening non-conductive layers.

While it may be well known to provide a source of electrical power for enhancing tissue healing/regeneration, dedicated devices for generating electrical potential add to the overall cost and complexity of an orthopedic implant procedure. Furthermore, with respect to implanted batteries, the increased cost of using such batteries also results in a greater invasive procedure because the batteries must be separately implanted and monitored over time.

As orthopedic procedures continue to advance in the types and diversity of fixation devices used to repair damaged tissue, the cost of employing such fixation devices often becomes the limiting factor in whether the particular procedure can be conducted within cost limits allowed by the insurance carrier. The addition of a separate electrical generating device or a complex combination of an integral electrical generating device within a fixation device are not viable solutions in the present day medical care systems.

Therefore, there is a need to combine an orthopedic fixation device with an electrical energy source in a reliable, cost effective design. There is also a need to provide such a combination that has multiple potential uses for differing medical procedures without requiring complete re-design of the combination. There is also a need to provide such a combination that can deliver selected electrical energy parameters within a single implant. There is yet further a need to provide a fixation device that can be used also as an anchor for traditional sutures for repair of soft tissues, while the anchoring device can also perform its traditional function of anchoring the sutures.

These needs are satisfied with the present invention as described below with respect to preferred embodiments of the invention.

SUMMARY OF THE INVENTION

In accordance with the present invention, bioelectric implants and methods are provided to include orthopedic fixation devices in the form of bioelectric implants especially adapted for enhancing tissue healing, thereby improving the capability of the implant to stabilize bone and soft tissue.

In another aspect of the invention, it includes a bioelectric suture construction capable of independently delivering electrical energy to targeted tissue. This suture construction includes anode and cathode portions allowing the suture to also perform as a galvanic cell.

In another aspect of the invention, various methods are provided for repairing and stabilizing tissue for healing and regeneration.

In accordance with the bioelectric implant of the present invention, in a preferred embodiment, the bioelectric implant comprises a body having externally protruding features that hold the implant within targeted tissue. The protruding features may include flutes, threads, ribs and/or barbs. The use of threads or flutes thereby presents the implant in a shape similar to a bone screw. The body of the implant has a central opening or cavity that extends through a longitudinal axis of the implant. The central opening may extend completely through the implant or partially through the implant. The central opening exposes a material that acts as an anode, while the exterior surface of the apparatus acts as a cathode. One preferred material for the anode is magnesium that can be applied as a coating within the central opening. The cathode may be a titanium 6-4 material. Bodily fluids and tissue in contact with the implant act as an electrolyte thereby enabling the implant to undergo a galvanic reaction for generation of electrical energy. The magnesium anode undergoes an oxidation process, while the titanium cathode undergoes a reduction process. A flow of electrons occurs from the anode to the cathode as facilitated by the bodily fluid/tissue performing the electrolyte function. More specifically, the bodily fluids and tissue that serve as electrolytes for the galvanic cell created by the bioelectric implant of the present invention include, for example, interstitial, or intraosseous fluids. Thus, the implant acts as a battery or galvanic cell in which chemical energy is converted into electrical energy by the spontaneous chemical reactions that take place at the anode and cathode.

A plurality of perforations or apertures may be provided that extend completely through the body of the cathode into the central opening. These perforations can be placed along selected locations on the body resulting in the localized creation of electrical energy around the perforations since the anode and cathode materials are in close arrangement. A pattern of electrical energy can be created according to the spacing and number of perforations provided. If it is desired to provide electrical energy at just one particular location around the implant, then it is also contemplated that the implant would have no perforations, and would be a closed shape except for the central opening. The creation of electrical energy would therefore be concentrated around the opening in which electrons would first travel into the tissue located closest to the central opening.

In accordance with the present invention, it is contemplated that the characteristic intensity, spacing and general pattern of the electrical energy generated is to be controlled by the shape of the implant, as well as the size of the implant and the number of perforations. The electrical energy created can also be controlled based upon the selected anode and cathode materials. For example, one or more of the following parameters can be controlled so as to selectively control the flow of electrical energy about the bioelectric implant: (1) the distance between anode surface and cathode surface; (2) the types of material used for the anode surface and cathode surfaces; (3) the type of material used to separate the anode surface from the cathode surface; and (4) the number, size, and distribution of perforations, if any, extending through the body of the bioelectric implant.

It is well known that electrical current follows the path of least electrical resistance. The electrical field created by the anode surface interacts with the electrical field created by the cathode surface. The path where the resistance is least (which also depends upon the path where the interaction between the respective electrical fields is the greatest) is the path which will carry current. However, given the dynamic nature of fluids and the human body, this path of least resistance may change over time. Accordingly, it is one aspect of the present invention to provide a bioelectric implant that is designed to establish multiple possible electrical paths between the anode surface and cathode surface at strategically placed locations to increase the probability that electrical current will flow in a desired location or locations.

In one aspect of the present invention, the implant is made only of two materials, namely, the cathode material making up at least the outside surfaces of the implant and the anode material found in the cavity.

In another aspect of the invention, the implant may be made of more than two materials. For example, the anode and cathode portions of the implant can be separated by a non-conductive material or substrate, such as a relatively hard plastic, particularly polyethylene or high density polyethylene. Other examples of materials that may be used to separate the anode and cathode portions include any material or combination of materials that have a surface resistivity of at least $1 \times 10^{12}$ $\Omega$/sq or a volume resistivity of at least $1 \times 10^{11}$ $\Omega$-cm. As can be appreciated, however, electrical resistivity is temperature dependent, so the above-identified values may vary without departing from the scope of the present invention. In this aspect, the anode and cathode materials could be deposited on the cavity and the outer surface of the implant. For example, the anode and cathode materials could be applied by mechanical, thermal, and/or chemical processes such as vapor deposition.

Additionally, the perforations can be provided as a means to route sutures through the perforations for anchoring the sutures to the implant.

The bioelectric implant of the present invention may be a single, unitary piece, or may comprise two or more interlocking pieces, thereby providing an anchor of a desired size and length, as well as an implant that can generate differing electrical energy based upon the intended use of the implant in a specific medical procedure.

In another aspect of the invention, the sutures may provide their own electrical potential by providing a suture construction including a central core or strand that acts as an anode, and one or more helical wraps of dissimilar material that act as a cathode. In this aspect, the type of suture materials used, as well as the diameter of the core and wrapped strands of material can dictate the electrical potential generated by the bioelectric suture.

In yet another aspect of the invention, the bioelectric implant can be a system in which the implant comprises various components of hardware used for bone/tissue repair. One example of a system includes the use of one or more bioelectric bone screws and a bioelectric plate that is held in place by the bone screws. The bioelectric plate has openings to receive the bone screws. These openings or other openings on the plate may be coated with an anode material while the plate acts as a cathode. Electrical energy would therefore be created by a combination of the screws and the plate.

Other features and advantages of the present invention will become more apparent from a review of the figures, taken in conjunction with the detailed description.

DETAILED DESCRIPTION OF THE INVENTION

Figure 1:
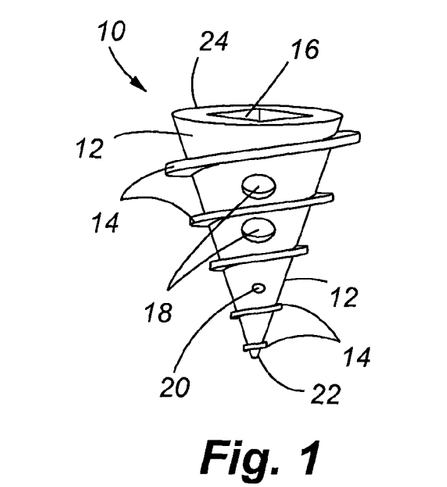
FIG. 1 is a perspective view of a first embodiment of the bioelectric implant of the present invention.

FIG. 1 illustrates a first embodiment of the bioelectric implant 10 of the present invention. The bioelectric implant 10 is characterized by a body 12 which comprises the cathode portion, and a central opening 16 that is coated with a dissimilar metal, thereby forming an anode portion. Preferred materials for the cathode may include titanium, steel, cobalt, molybdenum, metal oxides, or alloys thereof. Preferred materials for the anode portion may include magnesium, zinc, or alloys thereof.

The first embodiment is further characterized as having a larger end 24, and a smaller end or tip 22. The embodiment of FIG. 1 shows the body 12 having a substantially conical shape; however, it shall be understood that the particular shape of the body 12 may be modified for the intended use of the implant. For example, the body 12 could be cylindrical shaped, and further, instead of the tip 22 being closed, it is contemplated that the central opening 16 could extend completely through the body, thereby resulting in an opening located at both ends of the implant.

A plurality of flutes/threads 14 protrude from the outer surface of the body 12. The particular pitch, thickness, and width of the flutes 14 may be adjusted to match the particular requirements for the implant to be adequately anchored in the targeted tissue. The implant 10 is further characterized by a plurality of perforations 18 that extend completely through the body 12 thereby forming a passageway for bodily fluids/ tissue to interconnect the cathode portion to the anode portion. The perforations 18 may be selectively spaced around the periphery of the body 12 between the flutes. The number and size of perforations 18 may be selected to provide the desired electrical potentials generated at these locations. One or more suture openings 20 may also be formed in the body 12 which allows sutures to be secured to the implant 10, thereby enabling the implant to act as an anchor for the sutures. Sutures may also pass through the perforations 18.

Figure 2:
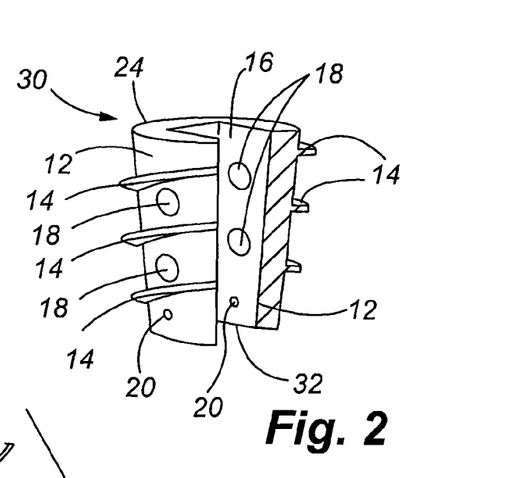
FIG. 2 is a fragmentary perspective view of a second preferred embodiment of the bioelectric implant also illustrating the central opening and perforations communicating with the central opening.

FIG. 2 illustrates another preferred bioelectric implant 30 in accordance with the present invention. Like reference numbers used in FIG. 2 correspond to the same structural elements in the first embodiment. The embodiment of FIG. 2 differs from the embodiment in FIG. 1 in that the body 12 has a truncated open end 32, and thus the central opening 16 extends completely through the implant.

Figure 3:
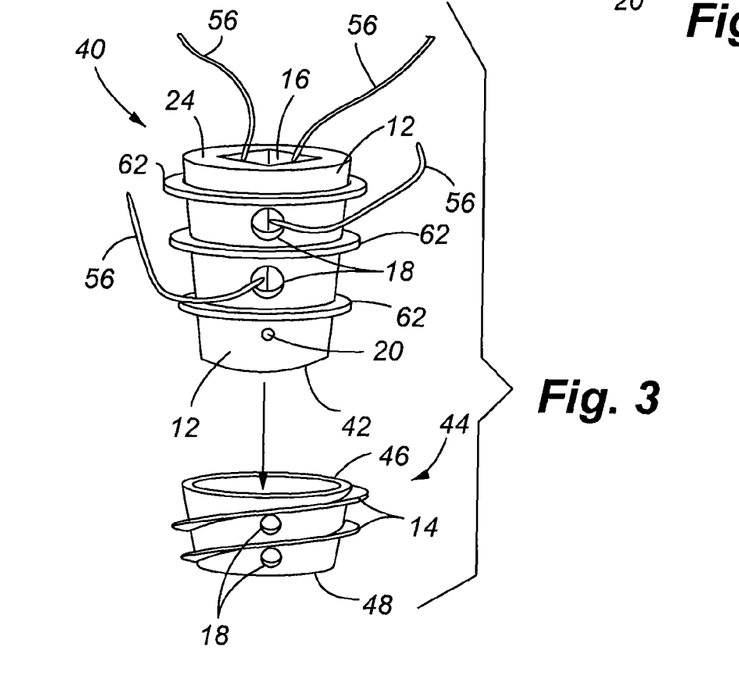
FIG. 3 is a perspective view of a third embodiment comprising a bioelectric implant having a multiple parts that can be joined to form a single larger implant.

FIG. 3 illustrates yet another preferred embodiment of an implant 40 of the present invention, like reference numbers in this embodiment also denoting the same structural features found in the prior embodiments. The implant 40 in this embodiment has two components or parts, namely, a distal lock ring 44, and a body 12 which resembles the body 12 in the embodiment of FIG. 2. However in this second embodiment, the body 12 incorporates a plurality of ribs 62 as opposed to threads 14. The ribs 62 are used to lock the body 12 in the distal locking ring 44. The ribs also serve as anchoring features. The locking ring 44 is connected to the body 12 to form a single larger implant. The body 12 includes the truncated end 42 which frictionally engages the receiving end 46 of the distal lock ring as by contact of one or more ribs 62 that are received within the central opening of the locking ring 44. The conical shape of the body 12 may be adjusted to provide contact with the desired number of ribs 62 in order to adequately lock the body to the locking ring. The diameter of the ribs may also be adjusted to provide the necessary frictional contact between the elements. The distal lock ring itself has a truncated end 48 which could be used to engage yet an additional distal lock ring (not shown) in the event the practitioner desired to have a series of three elements as the implant, for example, to increase the anchoring capability and/or the characteristics of the electrical energy to be generated. Thus, the embodiment of FIG. 3 allows a practitioner to adjust the size/length of the implant based upon the procedure to be conducted, and also allows the practitioner to alter the characteristics of the electrical energy created.

More specifically, if tissue growth is desired at a particular location relative to the implant 40, then the body 12 may be positioned in the receiving end 46 such that perforations 18 or suture openings 20 in the body 12 coincide with selected perforations 18 in the receiving end 46. If the two members are positioned such that a continuous opening is created from the outer surface of the implant 40 to the cavity 16, then current may be more likely to flow between the anode portion and the cathode portion. The current induced through such an opening may stimulate the desired tissue growth.

Additionally, the body 12 may be positioned relative to the receiving end 46 so as to close certain perforations 18, create larger perforations 18, and/or create smaller perforations 18. The larger perforations 18 may act to induce a greater amount of current (due to their relatively larger area) than will the smaller perforations 18. Conversely, if more current is desired to pass over the top surface or larger end 24 of the implant, then the perforations 18 may be selectively closed. Similarly, the distance between the anode portion and cathode portion may be adjusted by selectively controlling how far the body 12 is inserted into the receiving end 46, providing a finer degree of control over the electrical energy created by the implant 40.

Figure 4:
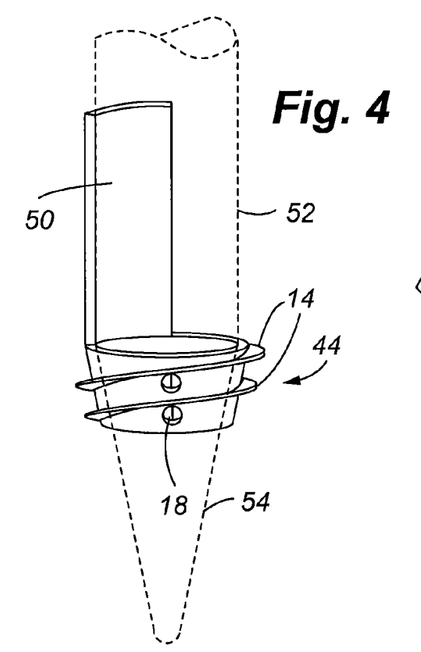
FIG. 4 is a perspective view of one part of the third preferred embodiment and an emplacement tool for positioning this part.

Referring to FIG. 4, another advantage with the embodiment of FIG. 3 is the ability for the practitioner to first emplace the distal lock ring at a desired location with the patient by use of an emplacement tool 52. The emplacement tool 52 may be in the form of a punch having a sharpened distal end 54 enabling the punch to penetrate soft tissue. The emplacement tool 52 is removed after placing the lock ring, and the body 12 of the implant is then positioned to frictionally engage the lock ring.

Figure 5:
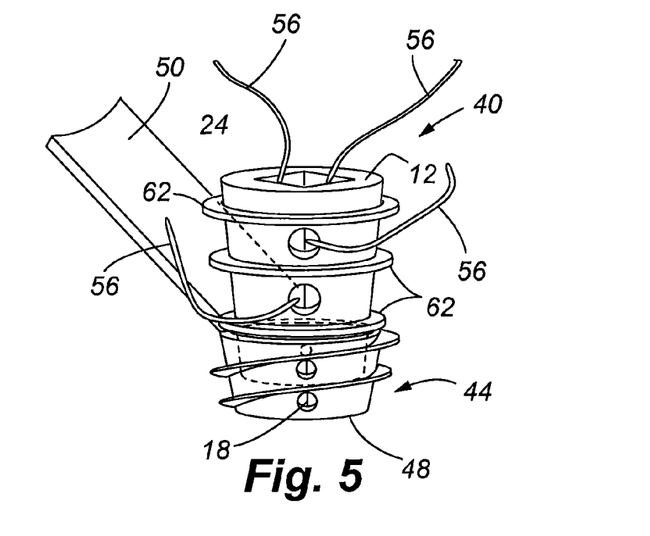
FIG. 5 is a perspective view of the third embodiment showing two parts joined to form the single larger implant, and a tab of one part being broken away.

Referring to FIG. 5, optionally, the distal lock ring 44 may include a tab 50 which provides better support for engagement between the emplacement tool 52 and lock ring 44 during emplacement of the lock ring. The emplacement tool 52 can also be used to position the body 12 for engagement with the lock ring. The distal end 54 of the emplacement tool is inserted within the central opening 16 and the body 12 is then aligned with the distal lock ring 44. Once the body 12 and distal lock ring have been joint, the implant can be rotated to allow the flutes to engage the tissue/bone for final emplacement of the implant.

Figure 6:
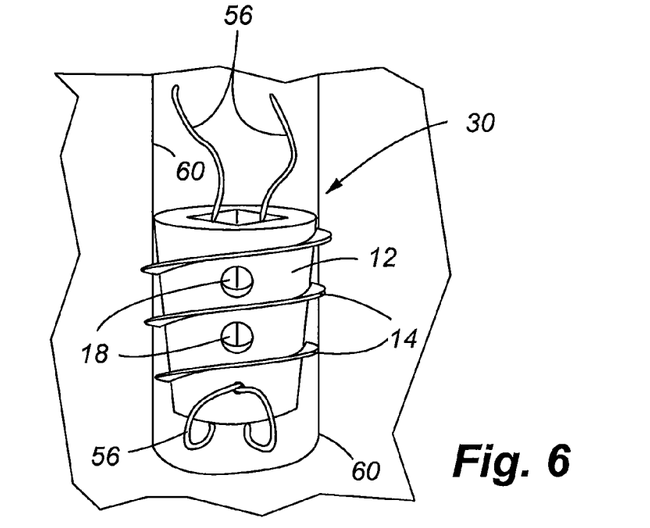
FIG. 6 is a perspective view of the second embodiment as it has been emplaced within the body, such as within a bone tunnel.

Referring to FIG. 6, it is also contemplated that the bioelectric implants of the present invention are ideally suited for emplacement within a pre-drilled bone tunnel. As shown in the example of FIG. 6, the implant 30 has been positioned within a bone tunnel in which the flutes/threads 14 engage the bone tunnel walls 60.

FIGS. 3, 5 and 6 also illustrate sutures that can optionally be attached to the bioelectric implants. In FIGS. 3 and 5, the sutures are shown as extending through the perforations 18 and through the central opening 16. This suture configuration could be useful, for example, for routing of the sutures through soft tissue in which the implant serves as an anchor and the sutures are then arranged in a pattern and tied to one another or secured at their opposite ends to another implant. In the example of FIG. 6, the sutures are routed through the smaller suture opening 20, and back through the central opening 16 so that the sutures do not get trapped between the flutes and bone tunnel wall 60. The sutures 56 therefore pass through the bone tunnel and may be tied remotely on soft tissue covering the bone tunnel, or may be secured to another implant.

Figure 7:
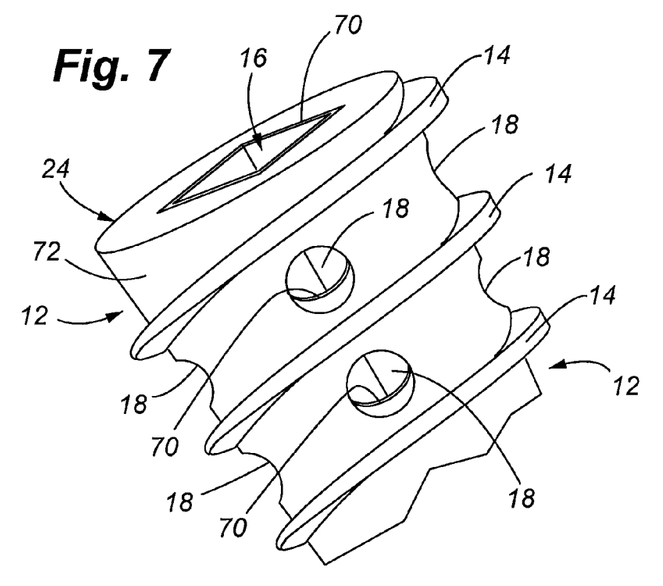
FIG. 7 is an enlarged fragmentary perspective view of the second embodiment illustrating the anode applied as a coating within the central opening.

FIG. 7 is an enlarged fragmentary perspective view of the bioelectric implant of FIG. 2. In this figure, the anode 70 has a definable thickness as compared to the body 12 which comprises the cathode 72. As mentioned, it is contemplated that the cathode could be a coating applied to an underlying substrate forming the body 12. The body 12 could be made of an insulating material such, or even another metallic material to facilitate a galvanic reaction. Therefore, the benefits of generation of electrical energy could be achieved, without the body 12 being involved within the galvanic reaction thereby better maintaining the body 12 as a structural anchoring device not subject to the deleterious effects of reduction. The body in this case could also act as an insulator to control discrete locations where galvanic reactions are to take place for purposes of isolating specific targeted tissue to be exposed to the electrical energy. The anode that undergoes oxidation does not affect the capability of the implant to serve as an anchor because the oxidation/corrosion is confined to the interior surface of the implant, i.e., the area within the central opening. Thus, the arrangement of the anode within the central opening is ideal for providing a combination anchoring device and electrical power source.

Figure 8:
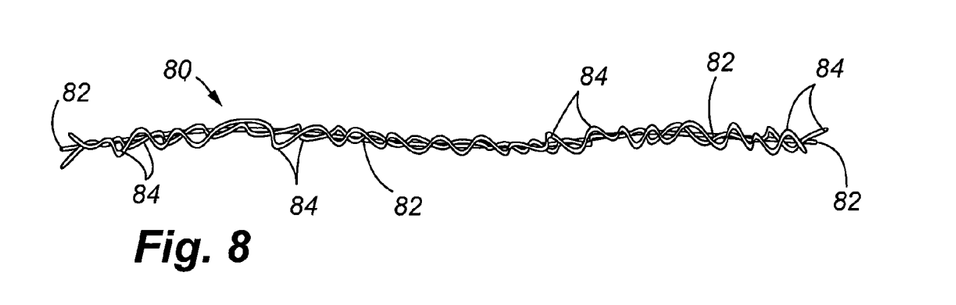
FIG. 8 is a perspective view of a first embodiment of the bioelectric suture of the present invention.

Referring to FIG. 8, in accordance with another aspect of the present invention, a bioelectric implant 80 is provided in the form of a suture having dissimilar metallic elements for creation of a galvanic cell that produces electrical energy. The bioelectric suture 80 comprises a central strand or core 82, and one or more peripheral strands 84 that may be wrapped around the core 82 in a helical fashion. The peripheral strands can also be wrapped in a more irregular pattern that provides additional anchoring capability for the suture. The core 82 function as the anode portion, and the peripheral strands 84 function as the cathode portion. Bodily fluids and tissue function as the electrolyte for facilitating the galvanic reaction to take place for generation of an electrical energy along the suture 80.

Figure 9:
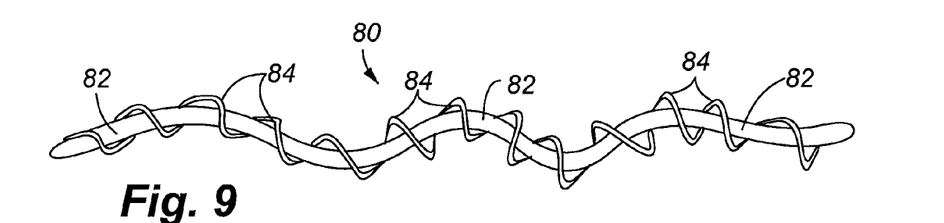
FIG. 9 is a perspective view of a second embodiment of the bioelectric suture of the present invention.

FIG. 9 illustrates another embodiment for the bioelectric suture 80. In this embodiment, the central core 82 has a greater diameter, and there is a single peripheral strand 84. Accordingly, assuming the materials are the same as between the embodiments in FIGS. 8 and 9, the electrical energy generated will have differences among the embodiments.

Figure 10:
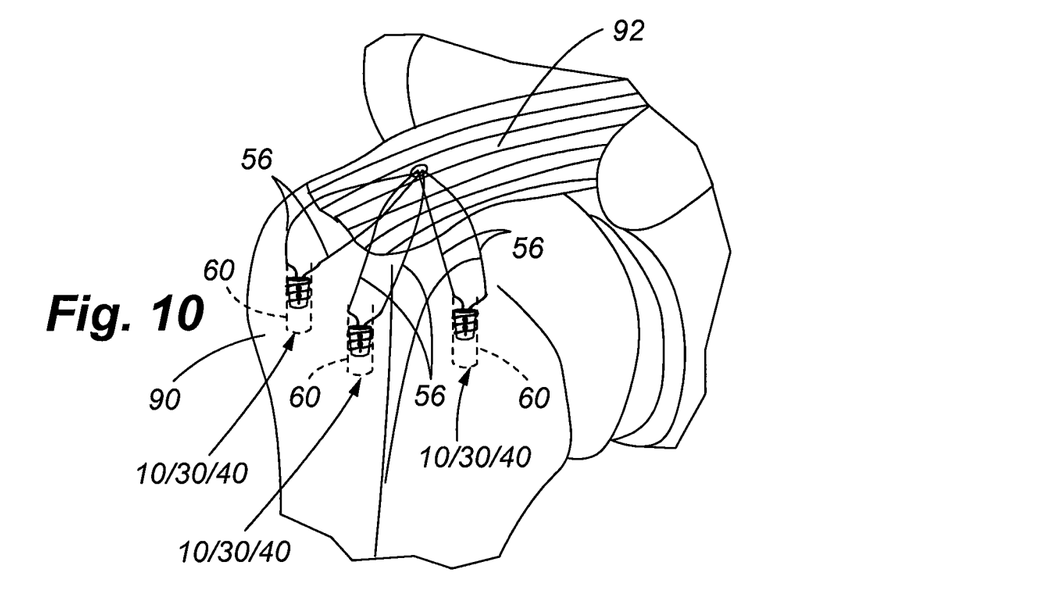
FIG. 10 is a perspective view of the bone and tissue structure involved with repair of a torn rotator cuff in which three bioelectric implants are used along with traditional sutures anchored by the implants.

FIG. 10 illustrates three bioelectric implants 10/30/40 for repair of a torn rotator cuff. More specifically, FIG. 10 illustrates three bioelectric implants that have been emplaced in selected soft tissue or bone locations 60 on the humeral head 90. Sutures 56 anchored by the implants extend over the greater tuberosity/musculature 92 of the rotator cuff. The sutures may be tied in a pattern determined by the practitioner and/or the free ends of the suture may be anchored to other bioelectric implants (not shown).

Figure 11:
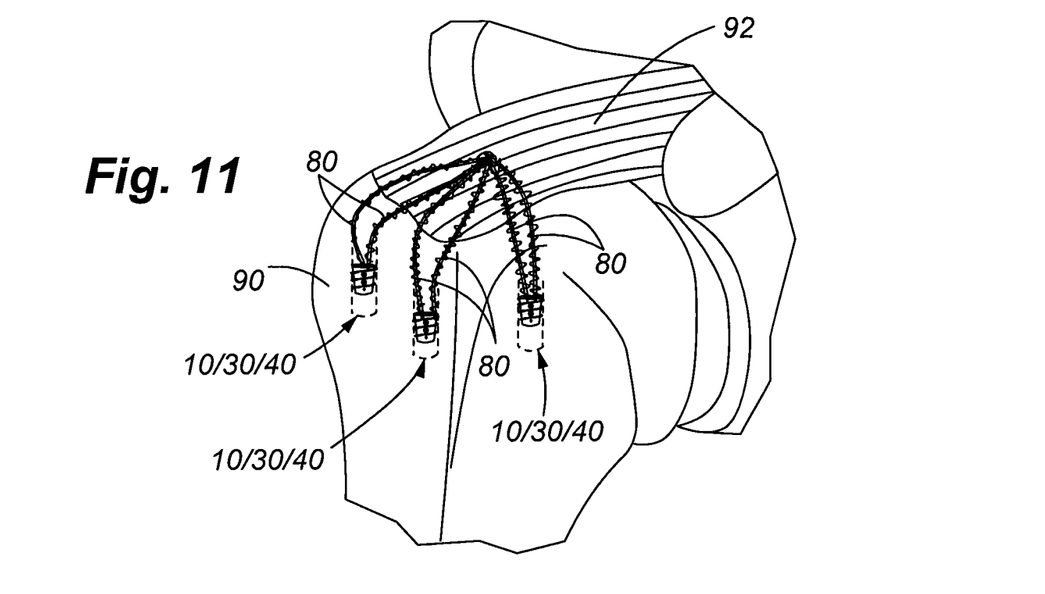
FIG. 11 is another perspective view of the bone and tissue structure involved with repair of a torn rotator cuff in which three bioelectric implants are used along with bioelectric sutures anchored by the implants.

FIG. 11 illustrates another configuration of bioelectric implants 10/30/40 that have been emplaced for repair of a torn rotator cuff. This configuration incorporates the bioelectric sutures 80. In FIG. 11, not only is an electrical energy generated by the implants 10/30/40, but there is supplemental electrical energy generated by the bioelectric sutures 80 thereby providing additional potential therapeutic benefit for the underlying soft tissue over which the sutures extend.

Figure 12:
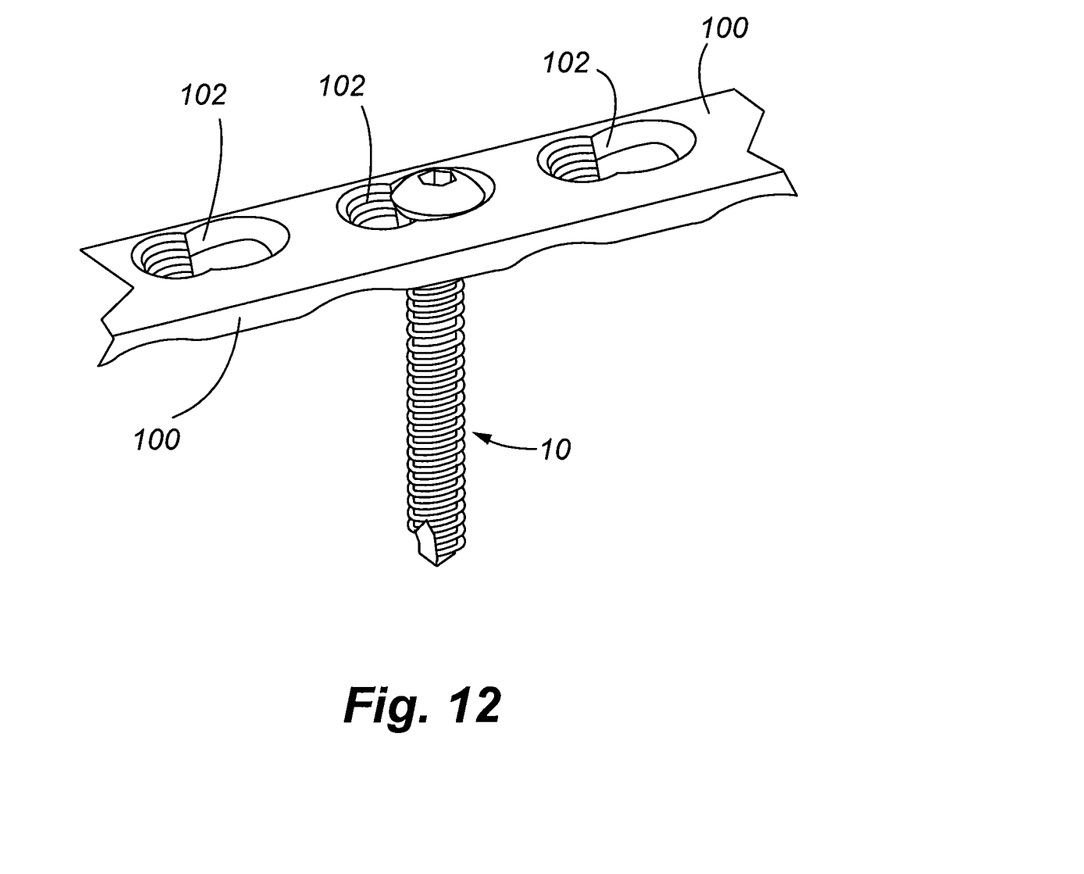
FIG. 12 is a perspective view of the system of the present invention in which bioelectric implants are provided in combination as a bone screw and a plate.

FIG. 12 illustrates the system of the present invention in terms of a combination of more than one type of implanted hardware. In the embodiment of FIG. 12, the system comprises one or more bioelectric anchors such as the implants 10/30/40 and a bioelectric plate 100, such as a compression plate that is used for stabilization and repair of a large bone mass. The bone screws are bioelectric capable and can be as described as one of the bioelectric implants discussed above. The bioelectric plate 100 can generate energy by constructing the plate of differing metals. The openings 102 in the plate can be coated with a material making the openings the anode, while the body of the plate can be the cathode. Selected openings 102 can be coated with the anode material in order to generate electrical energy at desired locations, to include openings that may or may not receive a bone screw.

The present invention provides bioelectric implants that generate electrical energy with desired characteristics in order to provide bone and soft tissue healing advantages. The electrical energy applied to, for example, poor bone quality areas, greatly enhances robust bone regeneration and healing of the soft tissues surrounding the bone. The electrical energy may be generated by a single implant, a group of implants, and in combination with bioelectric sutures.

There are many medical procedures that may have better clinical outcomes by using the bioelectric implants of the present invention. Although rotator cuff repair is one example provided, there are a great number of other procedures that may take advantage of the bioelectric implants. These other procedures may include: instability repair for glenoid and humeral head applications, spinal applications, craniomaxiofacial indications, endodontics, ACL reconstructions, tibial reinforcements and facial plastic surgery implants. Examples of orthopedic fixation devices that can be enhanced by the bioelectric implant constructions of the present invention include: shoulder anchors, trauma pins and plates, joint prothestis systems, spine pedicle screws and cages, ACL interference screws, ACL cross pin or cross screw devices, ACL posts, washers, or staple devices, craniomaxiofacial screws and plates, plastic surgery implants, foot and ankle anchors, pins, and plates, mesh or tissue reinforcements, and small joint screws and pins.

As mentioned, titanium 6-4 and magnesium are ideal materials to be used as the cathode and anode, respectively. Furthermore, additional coatings can be applied to the cathode portion, such as black platinum to modify the galvanic reaction. Corrosion occurring at the anode does not pose a problem either in terms of patient health or in terms of degradation of the implant as an anchor. Material such as Magnesium is a useful body mineral if administered in proper amounts. The corrosion is limited to the interior surface of the implant that does not affect the structural integrity of the implant. The corrosion products are magnesium ions, formerly electrically neutral ions that become positively charged after the oxidation process by electron migration to the cathode. The magnesium ions are absorbed in interstitial spaces within surrounding tissue, and therefore, the absorption of the ions enhances the capability of the tissue to act as an electrolyte since the magnesium ions are highly conductive.

Also as mentioned, it is contemplated within the present invention that the shape and size of the implants may be modified for directing or concentrating an electrical energy at targeted locations. For example, in the first embodiment, the sealed or closed smaller end of the implant would not generate electrical energy, and would only conduct current generated at another location along the cathode such as at the open end of the implant. Thus, the open end would presumably generate an electric current that would conduct the current more directly to the tissue surrounding the open end as opposed to tissue located at the smaller end.

Although the present invention has been described above with respect to preferred embodiments, various changes and modifications can be made to the invention commensurate with the scope of the claims appended hereto.

What is claimed is:

1. A bioelectric implant comprising:
   a body forming a cathode portion, said body having an external surface, and a plurality of protrusions including threads formed over the body and extending from said outer surface; said body further having a central opening formed therein defining a cavity;
   an anode portion formed within and exposed to said cavity, said anode portion being made of a dissimilar material as compared to said cathode portion,
   a plurality of perforations formed through said body and separated from said threads;
   said bioelectric implant forming a galvanic cell in which bodily fluids/tissue act as electrolytes to facilitate a galvanic reaction for production of electrical energy; and
   wherein said cavity remains open such that said bodily fluids/tissue contact said body including said cavity.

2. An implant, as claimed in claim 1, further including:
   at least one suture routed through a perforation of said plurality of perforations.

3. An implant, as claimed in claim 1, wherein:
   said body has a first part and second part, said first part having first and second ends, and said second part having first and second ends, said second end of said first part engaging said first end of said second part.

4. An implant, as claimed in claim 3, further including:
   a tab extending away from said second part, and said tab extending exteriorly from and adjacent to said first part.

5. A bioelectric implant comprising:
   a body forming a cathode portion, said body having an external surface, and a plurality of protrusions extending from said outer surface; said body further having a central opening formed therein defining a cavity;
   an anode portion formed within said cavity, said anode portion being made of a dissimilar material as compared to said cathode portion,
   a plurality of perforations formed through said body;
   wherein said bioelectric implant forms a galvanic cell in which bodily fluids/tissue act as electrolytes to facilitate a galvanic reaction for production of electrical energy; and
   a bioelectric suture contacting said bioelectric implant, said bioelectric suture including a core forming an anode portion, and at least one peripheral member forming a cathode portion, wherein said bioelectric suture generates electrical energy by contact of said suture with bodily fluids/tissue that acts as an electrolyte.

6. An implant, as claimed in claim 1, wherein:
   said anode portion is formed as a coating upon a portion of said body within said cavity.

7. A method of generating electrical energy for purposes of healing/regeneration of tissue, said method comprising:
   a body forming a cathode portion, said body having an external surface, and a plurality of protrusions extending from said outer surface; said body further having a central opening formed therein defining a cavity;
   an anode portion formed within and exposed to said cavity, said anode portion being made of a dissimilar material as compared to said cathode portion,
   a plurality of perforations formed through said body; and
   emplacing the bioelectric implant in tissue of a patient; and
   generating an electrical field by bodily fluids/tissue acting as an electrolyte to create a galvanic cell wherein a galvanic reaction takes place between the anode and cathode portions of said bioelectric implant, and wherein said cavity remains open such that said bodily fluids/tissue contact said body including said cavity.

8. A method, as claimed in claim 7, further including:
   adjusting the location where the electrical energy is produced by selecting a number, size, and distribution of perforations.

9. A method, as claimed in claim 7, further including:
   adjusting the potential of the electrical energy by selecting different anode and cathode materials.

10. An implant, as claimed in claim 1, further including:
    an insulating element positioned between said anode portion and said cathode portion to control the location of galvanic reactions to take place thereby isolating targeted tissue to receive electrical energy.

11. A method, as claimed in claim 7, wherein:
    said anode portion is formed as a coating upon a portion of said body within said cavity.

* * * * *